United States Patent [19]

Sato et al.

[11] Patent Number: 4,666,929
[45] Date of Patent: May 19, 1987

[54] ANTHRANILIC ACID ESTER DERIVATIVES AND ANTIINFLAMMATORY AND ANALGETIC EXTERNAL PREPARATIONS CONTAINING THE SAME

[75] Inventors: Yoshihisa Sato; Tetsuji Hirao; Tsunao Magara; Kohya Shiratori, all of Yokohama, Japan

[73] Assignee: Shiseido Company Ltd., Tokyo, Japan

[21] Appl. No.: 847,783

[22] Filed: Apr. 3, 1986

[30] Foreign Application Priority Data

Apr. 10, 1985 [JP] Japan .................. 60-76300
Nov. 26, 1985 [JP] Japan .................. 60-265713

[51] Int. Cl.⁴ ............... C07D 213/55; C07D 307/54; A61K 31/44; A61K 31/34
[52] U.S. Cl. .................. 514/357; 514/471; 546/335; 549/499
[58] Field of Search .............. 546/335; 549/499; 514/357, 471

[56] References Cited

FOREIGN PATENT DOCUMENTS 2145081A 3/1985 United Kingdom ............ 514/343

*Primary Examiner*—Alan L. Rotman
*Attorney, Agent, or Firm*—Sprung Horn Kramer & Woods

[57] ABSTRACT

Anthranilic acid ester derivatives having the general formula (I):

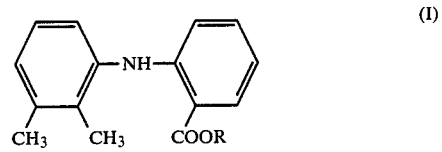

wherein R represents as alkyl group having 1 to 3 carbon atoms substituted with a pyridyl group or a furanmethyl group. These anthranilic acid ester derivatives have a remarkable antiinflammatory and analgetic effect and a high endermic permeability and, therefore, is suitable for use as an antiinflammatory and analgetic agent.

4 Claims, No Drawings

ANTHRANILIC ACID ESTER DERIVATIVES AND ANTIINFLAMMATORY AND ANALGETIC EXTERNAL PREPARATIONS CONTAINING THE SAME

BACKGROUND OF THE INVENTION

1. Field of the Invention

The present invention relates to novel anthranilic acid ester derivatives having the general formula (I):

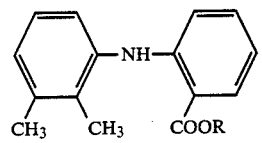

wherein R represents an alkyl group having 1 to 3 carbon atoms substituted with a pyridyl group or a furanmethyl group and external preparations containing the same having a remarkable antiinflammatory and analgesic effect.

2. Description of the Related Art

The anthranilic acid ester derivatives having the general formula (I) are novel compounds not reported in any publication at this time.

N-(2,3-xylyl)anthranilic acid, a mother compound of the anthranilic acid ester derivatives according to the present invention, is generally called mefenamic acid, and is widely used as an anti-inflammatory, antirheumatic, and antipyretic and analgetic agent. However, it is very difficult to dissolve N-(2,3-xylyl)anthranilic acid in, for example, water, an alcohol, or an oil and, therefore, it is used solely as an oral agent or medicine in the dosage form of a powder, tablet, or capsule. Thus, heretofore N-(2,3-xylyl)anthranilic acid has not been used as a skin treatment agent or as a topically or percutaneously applicable medicine. Furthermore, it is known that, when N-(2,3-xylyl)anthranilic acid is orally administered, various side effects including enterogasteric disorders, renal disorders, and vertigo occur.

SUMMARY OF THE INVENTION

Accordingly, the objects of the present invention are to eliminate the above-mentioned disadvantages and to provide a novel N-(2,3-xylyl)anthranilic acid ester derivative having an improved safety, endermic permeability, and affinity to the skin, and having a remarkable antiinflammatory and analgetic activity.

Another object of the present invention is to provide antiinflammatory and analgesic external preparations having a remarkable antiinflammatory and analgesic effect suitable for topical application to the skin.

Other objects and advantages of the present invention will be apparent from the following description.

In accordance with the present invention, there is provided anthranilic acid ester derivatives having the above-mentioned general formula (I).

In accordance with the present invention, there is also provided antiinflammatory and analgetic external preparations comprising, as an active component, anthranilic acid ester derivatives having the general formula (I).

DESCRIPTION OF THE PREFERRED EMBODIMENTS

The novel N-(2,3-xylyl)anthranilic acid ester derivatives having the general formula (I) according to the present invention are soluble in organic solvents such as, for example, hydrocarbons such as hexane and benzene, alcohols such as ethyl alcohol and propyl alcohol, and ketones such as acetone and methyl ethyl ketone.

The novel pyridylalkyl-N-(2,3-xylyl)anthranilates having the general formula (I), in which R represents an alkyl group having 1 to 3 carbon atoms substituted with a pyridyl group, are in the form of a pale yellow crystal. On the other hand, the novel 2-furanmethyl-N-(2,3-xylyl)anthranilate having the general formula (I) in which R represents a furanylmethyl group

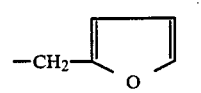

is in the form of a white crystal.

The N-(2,3-xylyl)anthranilic acid ester derivatives having the general formula (I) can be prepared by any conventional acid esterification reaction method. For example, the N-(2,3-xylyl)anthranilic acid ester derivatives (I) can be prepared by reacting N-(2,3-xylyl)anthranilic acid or the halides thereof with a pyridylalkyl alcohol or furfuryl alcohol, or by reacting the alkali salts of N-(2,3-xylyl)anthranilic acid with the halides of pyridylalkyl alcohol or 2-methyl halides of furan.

The alkyl moieties of the pyridylalkyl groups include methyl, ethyl, n-propyl, and iso-propyl moieties, preferably methyl and ethyl moieties, since the desired antiinflammatory activity tends to decrease with the increase in the carbon number of the alkyl moiety.

The N-(2,3-xylyl)anthranilic acid ester derivatives having the general formula (I) include:
2-pyridylmethyl-N-(2,3-xylyl)anthranilate,
3-pyridylmethyl-N-(2,3-xylyl)anthranilate,
4-pyridylmethyl-N-(2,3-xylyl)anthranilate,
2-(2-pyridyl)ethyl-N-(2,3-xylyl)anthranilate,
2-(3-pyridyl)ethyl-N-(2,3-xylyl)anthranilate,
2-(4-pyridyl)ethyl-N-(2,3-xylyl)anthranilate,
2-(2-pyridyl)propyl-N-(2,3-xylyl)anthranilate,
2-(3-pyridyl)propyl-N-(2,3-xylyl)anthranilate,
2-(4-pyridyl)propyl-N-(2,3-xylyl)anthranilate,
3-(2-pyridyl)propyl-N-(2,3-xylyl)anthranilate,
3-(3-pyridyl)propyl-N-(2,3-xylyl)anthranilate,
3-(4-pyridyl)propyl-N-(2,3-xylyl)anthranilate, and,
2-furamethyl-N-(2,3-xylyl)anthranilate.

The novel N-(2,3-xylyl)anthranilic acid ester derivatives having the general formula (I) according to the present invention can be either orally or parenterally administered or applied. That is, the present compounds can be in the form of, for example, tablets, capsules, powder, granules, and syrup in the case of oral administration, a suppository in the case of rectal administration, and ointments, cream, dermatologic paste, cataplasm, liquid, aerosol, and gel, in the case of external skin applications.

Especially since the novel N-(2,3-xylyl)anthranilic acid ester derivatives according to the present invention are readily soluble in organic solvents such as, for example, alcohols such as ethyl alcohol and propyl alcohol, and ketones such as acetone and methyl ethyl ketone, and are highly compatible with cream bases such as polyols, liquid paraffins, and ester oils as well as ointment bases such as petrolatum and lanolin, the present compounds can be advantageously formulated into externally applicable skin treatment compositions. This is also preferable because the present compounds have an excellent endermic permeability. When the present compounds are topically applied to the skin as a skin treatment composition, a remarkable antiinflammatory effect is exhibited and an excellent analgesic is also exhibited against concomitant pain. Thus, the N-(2,3-xylyl)-anthranilic acid ester derivatives according to the present invention are remarkably effective for use against acute eczema, chromic eczema, atopic dermatitis, contact-type dermatitis, zoster, various eczematoid dermatitis, various wounds, acne vulgaris, ambustion, acute and chronic arthritis, periarthritis, lumbago, and sarcitis.

Although the administration or application amount of the antiinflammatory and analgetic agent according to the present invention can be widely varied depending upon, for example, ages, individuals, and disease conditions, it is preferably 1 to 400 mg/kg/day in the case of the oral administration and, preferably, 0.01 to 100 mg/kg/day, more preferably 0.1 to 10 mg/kg/day, in the case of topical application. In either case, the agent can be administered or applied once or several times a day.

EXAMPLES

The present invention will now be further illustrated by, but is by no means limited to, the following Examples.

Synthetic Example 1

A 2.36 g amount of sodium N-(2,3-xylyl)anthranilate was dissolved in 20 ml of dimethyl formamide and 1.25 g of 2-chloromethyl pyridine was then added thereto. The mixture was allowed to react at a temperature of 90° C. for 3 hours. After the reaction, the solvent was distilled off in vacuo and the residue was charged with water. The mixture was then extracted with ether. After dehydration, the ether was distilled off and the resultant residue was recrystallized from methanol. Thus, 3.00 g of the desired pale yellow 2-pyridylmethyl-N-(2,3-xylyl)anthranilate having the following physical properties was obtained.

m.p.: 63°–64° C.

Elemental analysis: $C_{21}H_{20}O_2N_2$: Calc (%) C 75.88; H 6.07; N 8.43. Found (%) C 76.02; H 5.92; N 8.39.

Mass spectrum parent ion (m/e) = 332

Synthetic Example 2

A 2.41 g amount of N-(2,3-xylyl)anthranilic acid and 3.6 g of thionyl chloride were mixed in 20 ml of benzene and the mixture was reacted under reflux for 3 hours. The solvent and the extra thionyl chloride were distilled off. The residue was then charged with 50 ml of tetrahydrofuran and 1.37 g of 3-(4-pyridyl) propanol, followed by a gradual addition of 1.5 g of triethylamine while stirring at room temperature. The mixture was stirred for 30 minutes and was then allowed to react under reflux for one hour. After the reaction, the solvent was distilled off in vacuo and the residue was charged with water. The mixture was then extracted with ether. The oily residue thus obtained was recrystallized from methanol, and as a result, the desired pale yellow 3-(4-pyridyl)propyl-N-(2,3-xylyl) anthranilate having the following physical properties was obtained.

m.p.: 56°–57° C.

Elemental analysis: $C_{23}H_{24}O_2N_2$ : Calc (%) C 76.64; H 6.71; N 7.77. Found (%) C 76.51; H 6.43; N 7.58.

Mass spectrum parent ion (m/e) = 360.

Synthetic Examples 3 to 6

The following compounds listed in Table 1 were prepared in the same manner as in Synthetic Examples 1 and 2.

TABLE 1

| Synthetic Example No. | Compound | m.p. (°C.) | Mass spectrum parent ion (m/e) |
|---|---|---|---|
| 3 | 3-Pyridylmethyl-N-(2,7-xylyl)anthranilate | 65–66 | 332 |
| 4 | 4-Pyridylmethyl-N-(2,3-xylyl)anthranilate | 106–107 | 332 |
| 5 | 2-(2-pyridyl)ethyl-N-(2,3-xylyl)anthranilate | 55–56 | 346 |
| 6 | 3-(2-pyridyl)propyl-N-(2,3-xylyl)anthranilate | Pale yellow oily product more than 100° C. (decomposition) | 360 |

Synthetic Example 7 A 25.3 g amount of sodium N-(2,3-xylyl)anthranilate was dissolved in 200 ml of dimethylformaldehyde and 11.7 g of 2-chloromethyl furan was then added. The mixture was allowed to react at a temperature of 90° C. for 3 hours. After the reaction, the solvent was distilled off in vacuo, the residue was charged with water, and the mixture was then extracted with diethyl ether. After dehydration, the ether was distilled off and the resultant residue was recrystallized from ethanol. Thus, 28.3 g of white crystal 2-furanmethyl-N-(2,3-xylyl)anthranylate having the following physical properties was obtained.

m.p.: 50°–51° C.

Elemental analysis: $C_{20}H_{19}NO_3$. Calc (%) C 74.75; H 5.96; N 4.36. Found (%) C 75.12; H 5.92; N 4.29.

Mass spectrum parent ion (m/e) = 321

Synthetic Example 8

A 24.1 g amount of N-(2,3-xylyl)anthranilic acid was dissolved in 220 ml of dichloromethane and 22.7 g of N,N'-dicyclohexylcarbodiimide was added. The mixture was stirred for 30 minutes and 1.48 g of 4-pyrrolidinopyridine and 10.8 g of furfuryl alcohol were then added thereto. The mixture was stirred at room temperature for 5 hours.

After the reaction, the mixture was filtered and the solvent of filtrate was evaporated in vacuo. The residue was recrystallized from ethanol. Thus, 28.2 g of the desired white crystal 2-furanmethyl-N-(2,3-xylyl)anthranilate having following physical properties was obtained.

m.p.: 50°–51° C.

Mass spectrum parent ion (m/e) = 321

Evaluation Test Results

The N-(2,3-xylyl)anthranilic acid ester derivatives were evaluated with respect to the toxicity and pharmacological activities thereof.

Evaluation Test Example 1 (Acute Toxicity)

The evaluation test was carried out using ddY male mice (i.e., body weight = 18 to 22 g, 10 mice in each group).

The sample compound listed in Table 2 was dispersed in 0.5% carboxymethyl cellulose/physiological saline solution and orally administered in a given amount by a peroral syringe. After the administration, the toxic conditions were observed and the oral acute toxicity ($LD_{50}$) was calculated from the death number during 7 days of observation according to a Litchfield Wilcoxon method.

The results are shown in Table 2, in which the compounds are shown by R in the general formula (I). The compound represented by R=H in Table 2 is a known reference compound, i.e., N-(2,3-xylyl)anthranilic acid.

TABLE 2

| Compound (—R) | $LD_{50}$ |
|---|---|
| —H | 1400 mg/kg |
| 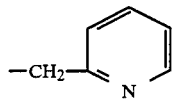 | 4425 mg/kg |
| 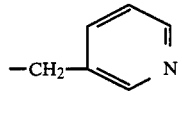 | 3825 mg/kg |
| 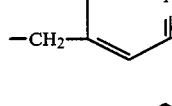 | 4850 mg/kg |
| 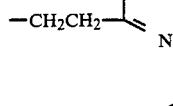 | 4100 mg/kg |
| 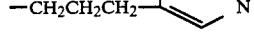 | 3750 mg/kg |

As is clear from the results shown in Table 2, the $LD_{50}$ of the compounds according to the present invention is about three times higher than that of the known N-(2,3-xylyl)anthranilic acid. Thus, the toxicity of the present compounds is very low.

Evaluation Test Example 2 (Acute Toxicity)

The evaluation test was carried out using ICR female mice (i.e., body weight=18 to 22 g, 10 mice in each group).

The sample compounds listed in Table 3 were dispersed in 2.0% carboxymethyl cellulose/physiological saline solution and orally administered in a given amount by a peroral syringe. After the administration, the toxic conditions were observed and the oral acute toxicity ($LD_{50}$) was calculated from the death number according to a Van Der Werden method.

The results are shown in Table 3.

TABLE 3

| Compound | $LD_{50}$ |
|---|---|
| N—(2,3-xylyl)anthranilic acid* | 1250 mg/kg |
| 2-furanmethyl-N—(2,3-xylyl)anthranilate | 5480 mg/kg |

*Reference compound

As is clear from the results shown in Table 3, the $LD_{50}$ of the present compound, i.e., 2-furanmethyl-N-(2,3-xylyl)anthranilate, is about 4 times higher than that of the known N-(2,3-xylyl)anthranilic acid. Thus, the toxicity of the present compound is very low.

Evaluation Test Example 3 (Antiinflammatory Activity)

The antiinflammatory effects of the present compounds were determined according to the so-called rat/carrageenan foot pad edema method. This method is admitted as a standard test method for determining antiinflammatory effects, because this method has a high correlationship with human antiinflammatory effects.

The evaluation test was carried out using Wister male rats (i.e., body weight =110–130 g, 8 rats in each group) according to a Winter et al method set forth in "Proceedings of the Society for Experimental Biology & Medicine, 111, p 554, 1962).

The sample compounds listed in Table 4 were dispersed in a 0.5% aqueous carboxymethyl cellulose solution and orally administered in a dosage of 100 mg/kg. One hour after the administration, 0.1 ml of a 1% λ-carrageenan/physiological saline was subcutaneously applied to the foot pad of one paw of the rat as an inflammatory inducing substance. Thus, the edema was caused. The volumes of the foot pad were measured in the predetermined constant time period before and after the administration and the increase ($V_1$) in the volume was calculated. On the other hand, the increase ($V_0$) in the volume of the foot pad of the control rats, to which the aqueous 0.5% carboxymethyl cellulose solution containing no test sample compounds, was determined by injecting the λ-carageenan. Thus, the inhibition (%) of the carageenan edema was calculated as follows:

$$\frac{V_0 - V_1}{V_0} \times 100$$

The antiinflammatory activity is high when this value is large.

The results obtained 5 hours after the time of the λ-carageenan injection are shown in Table 4.

TABLE 4

| Compound (—R) | Administration amount (mg/kg) | Inhibition % |
|---|---|---|
| —H | 100 | 56.8% |
| 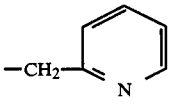 | 100 | 61.3% |
| 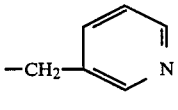 | 100 | 55.2% |

TABLE 4-continued

| Compound (—R) | Administration amount (mg/kg) | Inhibition % |
|---|---|---|
| —CH₂—[pyridyl]* | 100 | 53.5% |

*Reference compound, i.e., N—(2,3-xylyl) anthranilic acid

As is clear from the results shown in Table 4, the edema inhibitory activities of the N-(2,3-xylyl)anthranic acid ester derivatives according to the present invention are as strong as for the known N-(2,3-xylyl)anthranic acid (i.e., R=H in the general formula (I).

Evaluation Test Example 4 (Antiinflammatory Activity)

The evaluation test of 2-furanmethyl-N-(2,3-xylyl) anthranilate was carried out in the same manner as in Evaluation Test Example 3.

The results are shown in Table 5.

TABLE 5

| Compound | Administration amount (mg/kg) | Prevention % |
|---|---|---|
| N—(2,3-xylyl) anthranilic acid | 100 | 46.8% |
| 2-furanmethyl-N— (2,3-xylyl) anthranilate | 100 | 50.7% |

As is clear from the results shown in Table 5, the edema inhibitory activity of the present compound, i.e., 2-furamethyl-N-(2,3-xylyl)anthranilate, is as strong as for the known N-(2,3-xylyl)anthranilic acid.

Evaluation Test Example 5 (Antiinflammatory Activity)

The evaluation test of N-(2,3-xylyl) anthranilic acid derivatives was carried out according to the so-called ultraviolet erythema method.

Healthy Hartley strain albino guinea pigs (i.e., body weight=450–500 g, 10 pigs in each group) were used as the test animals. The back skin of the guinea pigs was clipped and shaved, and sections having a size of 1.41 cm × 1.41 cm were prepared in the back skin, by using a rubber plate, symmetrically spaced from the back center line. The divided sections were irradiated with ultraviolet ray having a medium wavelength (i.e., 280–320 nm, $\lambda_{max}$=305 nm) to induce erythema. After the UV irradiation, 10 μl of a solution of the test sample compound in olive oil was applied to the sections on one side. The formation of the erythema was observed over a period of time. The average erythema ($E_1$) in the section to which the sample compound was applied and the average erythema ($E_0$) in the section to which no sample compounds were applied were measured. From these results, the inhibition (%) of the UV induced erythema was calculated from the following equation.

$$\frac{E_0 - E_1}{E_0} \times 100 \, (\%)$$

When the inhibitory value (%) is large, the antiinflammatory activity of the sample compound is high. The results obtained 3 hours after the time of the UV irradiation are shown in Table 6.

TABLE 6

| Compound (—R*¹) | Application amount (μg/cm²) | Inhibition % |
|---|---|---|
| —H*² | 25 | 32.8% |
| —CH₂—[pyridyl] | 25 | 47.6% |
| —CH₂—[pyridyl] | 25 | 51.3% |
| —CH₂—[pyridyl] | 25 | 43.1% |
| —CH₂CH₂—[pyridyl] | 25 | 35.4% |
| —CH₂CH₂CH₂—[pyridyl] | 25 | 33.2% |

*¹R in the general formula (I)
*²Reference compound

As is clear from the results shown in Table 6, the novel N-(2,3-xylyl)anthranilic acid derivatives according to the present invention have antiinflammatory activities similar to or stronger than those of the known N-(2,3-xylyl)anthranilic acid.

Evaluation Test Example 6 (Antiinflammatory Activity)

The anti-inflammatory activity test of 2-furanmethyl-N-(2,3-xylyl)anthranilate was carried out in the same manner as in Evaluation Test Example 5.

The results are shown in Table 7.

TABLE 7

| Compound | Application amount (μg/cm²) | Prevention % |
|---|---|---|
| N—(2,3-xylyl) anthranilic acid* | 25 | 35.4% |
| 2-furanmethyl-N— (2,3-xylyl) anthranilate | 25 | 54.3% |

*Reference

As is clear from the results shown in Table 7, the 2-furanmethyl-N-(2,3-xylyl)anthranilate according to the present invention has an erythema stronger than that of the known N-(2,3-xylyl)anthranilic acid.

Evaluation Test Example 7 (Analgetic Activity)

The analgesic activity of the N-(2,3-xylyl)anthranilic acid derivatives according to the present invention was carried out by the so-called Randall-Selitto method set forth in Randall, L. O. and Selitto, J. J., "Archives of International Pharmacodynamics, 111, p 409 (1957). This method is admitted as a standard method for evaluating non-anesthetic analgesic agent.

The test sample compounds were applied to the both foot pad of hind paws of the rats each in an application amount of 50 μl as a 2.5% ethanol solution. After one hour, 50 μl each of the ethanol solution of the sample compound was again applied and 0.1 ml of a 5% brewer's yeast/physiological saline was immediately subcutaneously applied to one foot pad of the rat as a pain inducing substance. After a predetermined time period, the weight of the pain generation was measured using a horizontal balance type presser and the decrease rate ($P_1$) of the pain threshold value was determined. The above-mentioned evaluation test procedure was also carried out in the control rat group, except that the solvent containing no sample compounds was applied. Thus, the decrease rate ($P_0$) of the pain threshold value in the control group was determined. The inhibition (%) of the pain induced by the brewer's yeast was calculated as follows:

$$\frac{P_0 - P_1}{P_0} \times 100 \ (\%)$$

When this value is large, the analgetic activity is high.

The results obtained 5 hours after the time of the injection of the brewer's yeast are shown in Table 8.

TABLE 8

| Compound | Application amount | Inhibition % |
|---|---|---|
| N—(2,3-xylyl) anthranilic acid*[1] | 2.5 mg/paw | 32.8% |
| 2-(p-isobutylphenyl) propionic acid-2-pyridylmethyl ester*[2] | 2.5 mg/paw | 39.2% |
| 2-pyridylmethyl-N—(2,3-xylyl)anthranilate | 2.5 mg/paw | 53.6% |
| 3-pyridylmethyl-N—(2,3-xylyl)anthranilate | 2.5 mg/paw | 48.3% |
| 2-(2-pyridyl)ethyl-N—(2,3-xylyl) anthranilate | 2.5 mg/paw | 45.5% |
| 2-furanmethyl-N—(2,3-xylyl)anthranilate | 2.5 mg/paw | 56.5% |

*[1]known mother compound
*[2]Reference compound disclosed as an analgesic compound in U.S. Pat. No. 4150137

As is clear from the results shown in Table 8, the N-(2,3-xylyl)anthranilic acid ester derivatives according to the present invention exhibited excellent analgetic activities higher than those of the two reference compounds. Thus, the present compounds are clearly effective as an analgetic agent.

As is clear from the results shown in the above-mentioned Evaluation Test Examples, the N-(2,3-xylyl)anthranilic acid ester derivatives according to the present invention can be safely used as an antiinflammatory and analgetic agent.

| Formulation Example 1 (Ointment) | |
|---|---|
| Ingredient | Amount (g) |
| (1) 2-Pyridylmethyl-N—(2,3-xylyl) anthranilate | 2.5 |
| (2) Plastibase 50 W*[1] | 47.5 |
| | 50.0 |

*[1]a mixture of 95% liquid paraffin and 5% polyethylene.

The ingredient (1) was mixed in the ingredient (2), followed by degassing in vacuo. Thus, the ointment was formulated.

| Formulation Example 2 (Ointment) | |
|---|---|
| Ingredient | Amount (g) |
| (1) 2-Furamethyl-N—(2,3-xylyl) anthranilate | 2.5 |
| (2) Plastibase 50 W*[1] | 47.5 |
| | 50.0 |

*[1]see Formulation Example 1.

The ingredient (1) was mixed with the ingredient (2), followed by degassing in vacuo. Thus, the ointment was formulated.

| Formulation Example 3 (Cream) | |
|---|---|
| Ingredient | Amount (g) |
| (1) 3-Pyridylmethyl-N—(2,3-xylyl) anthranilate | 0.5 |
| (2) Cetastearyl alcohol | 2.0 |
| (3) Liquid paraffin | 20.0 |
| (4) Lanolin | 3.5 |
| (5) Stearyl monoglyceride | 1.1 |
| (6) Polyoxyethylene (20 mole) sorbitan monostearate | 1.4 |
| (7) 1,3-Butyrene glycol | 3.4 |
| (8) Ethyl paraben | 0.1 |
| (9) Distilled water | 18.0 |
| | 50.0 |

A mixture of the ingredients (1) to (6) was dissolved upon heating and the mixture having a temperature of 70° C. was added to the ingredients (7) to (9) at a temperature of 70° C., while stirring. The resultant mixture was treated in a homomixer to form fine emulsified particles and was then quenched while stirring.

Thus, the desired cream was formulated.

| Formulation Example 4 (Lotion) | |
|---|---|
| Ingredient | Amount (g) |
| (1) 3-(4-Pyridyl)propyl-N—(2,3-xylyl)anthranilate | 0.1 |
| (2) Glycerol | 4.0 |
| (3) 1,3-Butylene glycol | 4.0 |
| (4) Ethanol | 7.0 |
| (5) Polyoxyethylene oleyl alcohol | 0.5 |
| (6) Methyl paraben | 0.05 |
| (7) Citric acid | 0.01 |
| (8) Sodium citrate | 0.1 |
| (9) Purified water | 84.24 |
| | 100.00 |

The ingredient (2), (3), (7), and (8) were dissolved in the ingredient (9). On the other hand, the ingredinets (1), (5), and (6) were dissolved in the ingredient (4) and the resultant solution was added to the above aqueous solution to be solubilized. After filtration, the desired lotion was obtained.

| Formulation Example 5 (Dermatologic paste) | |
|---|---|
| Ingredient | Amount (g) |
| (1) 2-(3-Pyridyl)ethyl-N—(2,3-xylyl)anthranilate | 10.0 |
| (2) Zinc oxide | 12.0 |
| (3) Starch | 12.0 |
| (4) White vaselin | 16.0 |

-continued

| Formulation Example 5 (Dermatologic paste) | |
|---|---|
| Ingredient | Amount (g) |
| | 50.0 |

A portion of the ingredient (4) was dissolved on a water bath and was then charged with the ingredient (1). Thereafter, the resultant mixture was mixed with the ingredients (2) and (3), which were previously sifted through a 200 mesh sieve. After adding the remaining ingredient (4), the mixture was thoroughly mixed to obtain a uniform mixture. Thus, the desired dermatologic paste was formulated.

| Formulation Example 6 (Emulsion) | |
|---|---|
| Ingredient | Amount (g) |
| (1) Stearic acid | 2.5 |
| (2) Cetyl alcohol | 1.5 |
| (3) Vaseline | 5.0 |
| (4) Liquid paraffin | 10.0 |
| (5) 2-Furanmethyl-N—(2,3-xylyl) anthranilate | 1.0 |
| (6) Polyoxyethylene (10 mole) monooleate | 2.0 |
| (7) Polyethyleneglycol 1500*[1] | 3.0 |
| (8) Potassium hydroxide | 0.3 |
| (9) Purified water | Balance |
| (10) Perfume | q.s. |
| (11) Preservative | q.s. |
| | 100 |

The ingredients (7) and (8) were added to the ingredient (9) and the mixture (i.e., aqueous phase) was maintained at a temperature of 70° C. On the other hand, the remaining ingredients were mixed and were dissolved upon heating. The resultant oil phase was also maintained at a temperature of 70° C.

The oil phase was added to the aqueous phase and, after preemulsifying, the mixture was uniformly emulsified in a homomixer. After the emulsification, the emulsion was cooled to a temperature of 30° C. Thus, the desired emulsion was obtained.

The antiphlogistic and analgetic skin treatment compositions prepared in Formulation Examples 1 to 9 were stable with the elapse of time and exhibited excellent antiinflammatory and analgetic activities when the compositions were applied to the affected portions directly or via suitable fabrics, such as a gauze, having the compositions coated thereon.

We claim:

1. An anthranilic acid ester derivative having the general formula (I):

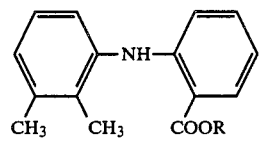

(I)

wherein R represents an alkyl group having 1 to 3 carbon atoms substituted with a pyridyl group or a furanmethyl group.

2. An anthranilic acid ester derivative as claimed in claim 1, wherein R in the formula (I) is an alkyl group having 1 to 3 carbon atoms substituted with a pyridyl group.

3. An anthranilic acid ester derivative as claimed in claim 1, wherein R in the formula (I) is a furanmethyl group.

4. An antiinflammatory and analgetic external composition comprising, as an active component, an effective amount of an anthranilic acid ester derivative having the general formula (I):

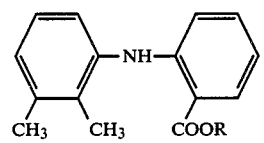

(I)

wherein R represents an alkyl group having 1 to 3 carbon atoms substituted with a pyridyl group or a furanmethyl group, in combination with an inert pharmaceutical carrier or adjuvant.

* * * * *